(12) United States Patent
Raman et al.

(10) Patent No.: US 10,092,004 B2
(45) Date of Patent: Oct. 9, 2018

(54) AGRICULTURAL ADJUVANTS AND PROCESSES FOR MAKING AND USING SAME

(71) Applicant: Celanese International Corporation, Irving, TX (US)

(72) Inventors: Narayan K. Raman, Cincinnati, OH (US); Hannah E. Toomey, Covington, KY (US); Kristin Herrel, Dallas, TX (US); Tatiana Craft, League City, TX (US); James Martin, Florence, KY (US); Erika Pedraza, Union, KY (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

(21) Appl. No.: 15/272,950

(22) Filed: Sep. 22, 2016

(65) Prior Publication Data

US 2017/0006859 A1 Jan. 12, 2017

Related U.S. Application Data

(63) Continuation-in-part of application No. 14/642,548, filed on Mar. 9, 2015.

(51) Int. Cl.
*A01N 57/20* (2006.01)
*A01N 25/30* (2006.01)
*A01N 25/06* (2006.01)

(52) U.S. Cl.
CPC ............. *A01N 57/20* (2013.01); *A01N 25/06* (2013.01); *A01N 25/30* (2013.01)

(58) Field of Classification Search
None
See application file for complete search history.

(56) References Cited

U.S. PATENT DOCUMENTS

| | | | |
|---|---|---|---|
| 4,104,220 A | 8/1978 | Sims | |
| 4,111,877 A | 9/1978 | Dixon et al. | |
| 4,219,454 A | 8/1980 | Iacoviello et al. | |
| 4,319,032 A | 3/1982 | Sandri et al. | |
| 4,599,417 A | 7/1986 | Sekmakas et al. | |
| 5,064,888 A | 11/1991 | Farwaha et al. | |
| 5,208,285 A | 5/1993 | Boyce et al. | |
| 5,530,056 A | 6/1996 | Farwaha et al. | |
| 6,093,856 A * | 7/2000 | Cripe ...................... | C07C 43/11 568/622 |
| 6,441,082 B1 * | 8/2002 | Weitzel ................. | C04B 24/163 524/458 |
| 7,070,795 B1 | 7/2006 | Botts et al. | |
| 2012/0238448 A1 | 9/2012 | Schneider | |
| 2013/0237419 A1 | 9/2013 | Shao et al. | |
| 2014/0162018 A1 | 6/2014 | Lunsford et al. | |

OTHER PUBLICATIONS

Non-Final Office Action received in U.S. Appl. No. 14/642,548, dated Dec. 15, 2016.
Fritz, B.K. et al. (2014). "Measuring Droplet Size of Agricultural Spray Nozzles—Measurement Distance and Airspeed Effects," *Atomization and Sprays* 24(9):747-760.
Non-Final Office Action received in U.S. Appl. No. 14/642,548, dated Dec. 22, 2017.
Immergut, E.H. et al. (Jan. 1, 1965). "Principles of Plasticization," Chapter 1 in *Plasticization and Plasticizer Processes*, Polytechnic Institute Brooklyn, N.Y., pp. 1-26.
O'Brien, J. (1988). "Plasticizers," in Modern Plastics Encyclopedia, McGraw Hill, New York, pp. 168-169.
Hallstar Technical Publication (Date unknown). "The Function and Selection of Ester Plasticizers," located at https://www.hallstar.com/webfoo/wp-content/uploads/The-Function-Selection-Ester-Plasticizers.pdf.

\* cited by examiner

*Primary Examiner* — Johann R Richter
*Assistant Examiner* — Danielle Sullivan
(74) *Attorney, Agent, or Firm* — Kilpatrick Townsend & Stockton LLP

(57) ABSTRACT

An agricultural spray pre-mix composition, comprising from 0.01 wt % to 40 wt % of an agricultural spray adjuvant comprising a vinyl ester-based or vinyl acrylate-based polymer dispersion and greater than 15 wt % of a plasticizer and from 1 wt % to 50 wt % of a water conditioning agent.

20 Claims, No Drawings

AGRICULTURAL ADJUVANTS AND PROCESSES FOR MAKING AND USING SAME

PRIORITY CLAIM

This application is a continuation-in-part of and claims priority to U.S. non-provisional patent application Ser. No. 14/642,548, filed on Mar. 19, 2015. The entirety of the application is incorporated by reference herein.

FIELD OF THE INVENTION

The present invention relates generally to agricultural spray mix pre-mix compositions, agricultural spray compositions, and processes for treating agricultural products using same. In particular, the present invention relates to agricultural spray mix pre-mix compositions comprising an aqueous polymer dispersion, a plasticizer, and a water conditioning agent.

BACKGROUND OF THE INVENTION

Adjuvants are generally known as substances that are added in crop protection sprays, e.g., herbicidal formulations or agricultural spray compositions, or to spray tanks used in the dispersion of same to improve activity of an active ingredient, e.g. a herbicide, that is also present in the crop protection spray or to improve application characteristics. Spray adjuvants are generally grouped into two broad categories: special purpose adjuvants and activator adjuvants. Special purpose adjuvants are typically know to widen the range of conditions under which a given crop protection spray is useful. The special purpose adjuvant may alter the physical characteristics of the spray solution. Exemplary special purpose adjuvants include compatibility adjuvants, buffering adjuvants, antifoam adjuvants, and drift control adjuvants. Exemplary special purpose adjuvant compounds include phosphatidylcholine, alkyl polyoxyethylene ether, methylacetic(acid), soluble polymers such as xanthum gum, rheology modifiers such as polyacrylamide (EDT Concentrate) and styrene butadiene latex emulsions. Exemplary commercial products include In-Place®, InterLock®, Bond®, LI700®, and Strikeforce™. Drift control adjuvants are employed to reduce or eliminate fine spray droplet particles ("fines" or "driftable fines") that are formed when the agricultural spray composition is sprayed, e.g., from an aircraft or a ground sprayer. Driftable fines are commonly defined as droplets that are less than 150μ, e.g., less than 105μ in size (droplet diameter). By reducing or eliminating driftable fines, drift control adjuvants allow more of the deployed agricultural spray composition to reach the intended target substrate. Because driftable fines are reduced, less of the deployed agricultural spray composition drifts away and damages adjacent vegetation. Some typical drift control adjuvants include crop oil concentrates (containing 80 to 85 percent of synthetic oil, 15-20 percent of surfactants), vegetable oil concentrates (containing 50-80 percent of vegetable oils and 20 to 50 percent nonionic surfactant), oil-in-water micro emulsions, and water-in-oil invert emulsions (made) with petroleum or vegetable oils, surfactants and water.

The oil-in-water micro-emulsions and water-in-oil invert emulsions are known to be essentially solvents or emulsifyable oils and typically have lower molecular weights, e.g., from 275 g/mole to 350 g/mole. Oil-in-water micro-emulsions and water-in-oil invert emulsions often contain a petroleum or vegetable derived oil that is immiscible with water and a surfactant to emulsify the mixture to make the oil and water miscible. These emulsions, however, do suffer from several disadvantages. For example, micro-emulsion droplets may be too large to spray. Also, the micro-emulsion may become unstable and phase separate over a time. The surfactants are known to produce foam during mixing especially with certain herbicides such as glyphosates. These drawbacks make it difficult to use such emulsions with conventional spray equipment without agitation. And in the case of large size droplets, large volumes of adjuvant are required to cover the pest infested target area. With the application of large volumes of pesticides applied to foliage, damage can be caused due to the toxic effect on the foliage by overconcentration of the emulsifers and/or oil in the large droplets applied.

Activator adjuvants are commonly used to enhance post-emergence active ingredient performance, e.g., herbicide performance. Activator adjuvants are known to increase activity, absorption into plant tissue, and rainfastness. Activator adjuvants can also decrease photodegradation of the active ingredient and also alter the physical characteristics of the spray solution. Activator adjuvants include surfactants, crop oil concentrates, nitrogen fertilizers, spreader-stickers, wetting agents, and penetrants. Although these conventional adjuvants may provide for some improvements in active ingredient and/or agricultural spray composition efficacy, the ability to reduce driftable fines is limited (often due to the high amount of surfactants that are necessarily used therewith). These high amounts of surfactants increase drift potential and increase phytotoxicity to the foliage. Some of the conventional adjuvants in particular have a limited effect on the median spray droplet size. In some cases, conventional adjuvants not only form greater amounts of driftable fines, but some of these conventional adjuvants also form greater amounts of very large droplets, e.g., greater than 730μ in size. In particular, soluble polymer based products such as polyacrylamide and xanthum gum are known to shift the entire distribution substantially to large droplet diameters and also increase relative span. The very large droplets may result in an agricultural spray composition that provides poor coverage due to rebound from the leaf surface, which in turn reduces the overall efficacy of the active ingredients. The soluble polymers also hydrate slowly and mix poorly, which leads to processing issues such as longer mixing times. And soluble polymers are also more susceptible to degrade under shear stress during application or pump transfer. Further, the required usage level for these adjuvants is often quite high, which results in unwanted phytotoxicity of the foliage due to the high surfactant concentration (as noted above).

In addition, some conventional drift reduction adjuvants have been known to have deleterious effects on the sticking and spreading of the agricultural spray composition on the intended substrate, e.g., leaf surfaces, which may result in reductions in the efficacy of the active ingredient and/or the agricultural spray composition as a whole. For example, some conventional drift reduction adjuvants can make the agricultural spray composition droplets evaporate or dry too quickly, which prevents absorption of the systemic herbicide into the leaf substrate. Also, some conventional adjuvants affect the surface tension of the agricultural spray composition such that spreading of the agricultural spray composition on the substrate, detrimentally, is limited.

Some vinyl ester-based polymer dispersions, e.g., stabilized polymer vinyl ester-based polymer dispersions, have been employed in a variety of applications including, for example, as binders for adhesives, paints and paper coating compositions. In these applications, the polymer dispersion may be used in combination with other components, e.g., plasticizers. In these cases, the polymer dispersions are present in higher concentrations, while the other components are present in lower concentrations. These concentrations are suitable for the respective application, but may not be suitable for different applications. While these polymer dispersions are known to be utilized with adhesives and paints, the use of the (vinyl ester-based) polymer dispersions in the crop protection milieu has not been contemplated.

The weight average molecular weight of these emulsions can range upwards from 250,000 g/mol to 400,000 g/mol. Importantly, these polymer dispersions differ significantly from the aforementioned oil-in-water micro-emulsions and water-in-oil invert emulsions, in both chemical composition and physical properties. For example, the oil-in-water micro-emulsions and water-in-oil invert emulsions have lower molecular weight oils and do not comprise polymers and/or the monomer precursors thereof, and, as a result, lack the defined structure of aqueous polymer dispersions. The weight average molecular weight of these emulsions can range upwards from 275 g/mol to 350 g/mol. Oil-in-water micro-emulsions and water-in-oil invert emulsions are not known to be used interchangeably with vinyl ester-based polymer dispersions.

In view of the shortcomings of conventional adjuvants, the need exists for new adjuvants that provide for improvements in overall agricultural spray composition efficacy, e.g., reductions in driftable fines and maintenance of the relative span of the droplet size.

SUMMARY OF THE INVENTION

In one embodiment, the present invention relates to an agricultural spray composition, comprising a vinyl ester-based polymer dispersion, a plasticizer, and an active ingredient (and optionally a liquid carrier, preferably water). The vinyl ester-based polymer dispersion may be stabilized, e.g., by at least one of a protective colloid and a surfactant, and preferably may comprise an aqueous dispersion of a polymer produced from one or more monomers, at least one of the monomers comprising a vinyl ester of a carboxylic acid. At least one of the monomers may comprise a vinyl ester of a carboxylic acid and having up to 20 carbon atoms. The plasticizer may be selected from the group consisting of an epoxidized methyl ester of soy oil, methyl ester of soy oil, triethylene glycol diester, polyalkylene glycols, polyether polyols, esters of canola oil, esters of castor oil, ester oils, 2,2,4-trimethyl-1,3-pentanediol monoisobutyrate, phthalates, adipic acid polyesters, trimellitates, adipates, epoxy esters, polyetheresters, epoxidized soy esters, benzoates, dipropylene glycol dibenzoate, diethylene glycol dibenzoate, and mixtures thereof (preferably being a triethylene glycol diester) and the active ingredient may be selected from the group consisting of herbicides, pesticides, fungicides, insecticides, acaricides, nematocides, foliar nutrients, defoliants, plant growth regulators, molluscidcides. Preferably, the active ingredient is selected from the group consisting of 2,4-D Dichlorophenoxyacetic acid (2,4-D), glyphosate, dicamba, triclopyr, imazapyr, sulfometuron, methyl, fluridone, clopyralid, picloram, hexazinone, chlorpyriphos, carbaryl, methomyl, ethepon, fosamine, benomyl, ferbam, zineb, and mixtures thereof. The active ingredient may be present in an amount from 0.5 to 5 wt %, based on total weight of the spray composition. The plasticizer may have a boiling point greater than 110° C. The invention may also relate to a method for producing an agricultural spray composition, comprising the steps of providing a vinyl ester-based polymer dispersion (optionally stabilized), adding to the vinyl ester-based polymer dispersion a plasticizer to form an adjuvant, and adding to the adjuvant an active ingredient to form the agricultural spray composition (and optionally adding to the adjuvant a liquid carrier). The adding may comprise adding to the vinyl ester-based polymer dispersion at least 15 wt % plasticizer. Preferably, the vinyl ester-based polymer dispersion is present in the adjuvant in an amount less than 85 wt %, based on the total weight of the adjuvant.

The vinyl ester-based polymer dispersion and the plasticizer may form an adjuvant and the adjuvant may be present in amount from 0.01 to 15 wt %, based on the total weight of the spray composition. The adjuvant may comprise greater than 15 wt % plasticizer and/or less than 85 wt % vinyl ester-based polymer dispersion. The plasticizer may be present in an amount from 15 wt % to 70 wt % based on the total weight of the adjuvant. The vinyl ester-based polymer dispersion may be a polymer produced from one or more monomers, at least one of the monomers comprising a vinyl ester of a carboxylic acid and having up to 20 carbon atoms, and may be stabilized by a protective colloid and/or a surfactant, and the one or more monomers may further comprise ethylenically unsaturated monomers capable of polymerizing with vinyl ester and ethylene. The vinyl ester preferably comprises vinyl acetate and the one or more monomers further comprise ethylene. The vinyl ester-based polymer dispersion may be protective colloid stabilized and the protective colloid is selected from the group consisting of hydroxyl ethyl cellulose, polyvinyl alcohol, polyethylene oxide, starch, and mixtures thereof (preferably hydroxyl ethyl cellulose) or the vinyl ester-based polymer dispersion may be surfactant stabilized and the surfactant is selected from the group consisting of one or more anionic and nonionic, amphoteric, and polymerizable surfactants. Preferably, the adjuvant has a pH from 3 to 8.5, and/or a static surface tension from 30 to 60 dynes/cm and/or a viscosity from 100 cp to 10000 cp. The adjuvant may be free of surfactant. The adjuvant may further comprise a viscosity modifying agent selected from the group consisting of polyvinyl alcohol, polyethylene oxides, polyethylene glycols, polypropylene glycols, cellulose derivatives, starches, attapulgites, synthetic clays, fumed silica, colloidal silica, hydrogenated castor wax, polyamide, carboxy functional acrylic, associative thickeners, alkali-swellable emulsions, alkali soluble emulsions, hydrophobically modified alkali-swellable emulsions, hydrophobically modified ethoxylated urethane resins, and mixtures thereof. The invention further contemplates a method for producing a spray adjuvant, comprising the step of providing a vinyl ester-based polymer dispersion, and adding to the vinyl ester-based polymer dispersion greater than 15 wt % of a plasticizer. Preferably, the vinyl ester-based polymer dispersion is present in an amount less than 85 wt %.

The invention further relates to a process for treating an agricultural product, comprising the steps of spraying on the agricultural product the agricultural spray composition, preferably forming droplets. Preferably, no more than 5 vol % of the droplets have a droplet size less than 105 μm and/or the droplets have an average droplet size from 50 μm to 1000 μm and/or the droplets have an average droplet size from 200 μm to 300 μm, and/or the droplets have an evaporation rate from 1% weight loss/min to 8% weight loss/min, and/or the rate of decrease in dynamic surface tension of the droplets is less than 10 mN/m-min, and/or the droplets have an average contact angle from 35° to 75°, and/or the spread diameter of the droplets ranges from 4.0 to 7.0 mm. The agricultural spray composition, when sprayed, may yield droplets having less than 7 wt % droplets less than 105µ in size, a relative span less than 1.2 and a Dv50 greater than 250µ.

In some embodiments, the invention relates to an agricultural spray pre-mix composition, comprising from 0.01 wt % to 40 wt % of an agricultural spray adjuvant and from 1 wt % to 50 wt % of a water conditioning agent. The adjuvant may comprise a vinyl ester-based or vinyl acrylate-based polymer dispersion and greater than 15 wt %, based on total weight of the adjuvant, of a plasticizer, e.g., from 15 wt % to 70 wt %. The water conditioning agent may comprise a compound selected from nitrogen-containing sulfates, (sulfur-containing) carboxylic acids, phosphate salts, and mixtures thereof. The pre-mix composition, shows a non-Newtonian rheology having a viscosity less than about 150 cp, as measured by a rotational rheometer and/or after at least two weeks of storage at 25° C., the pre-mix composition may show substantially no macro separation and/or when mixed with water at a volume ratio of 0.05 ounces/gallon to 1 ounce/gallon and after at least two weeks of storage at 25° C., the composition is a homogeneous dispersion. The pre-mix composition, when combined with water at a weight ratio of at least 95:1, may have a viscosity less than 5 cp as measured by a rotational rheometer. The pre-mix composition, in some cases, has a pH ranging from 2 to 8. The pre-mix composition may further comprise a surfactant present in an amount less than 15 wt % based on the total weight of the pre-mix composition, the surfactant may also be present in an amount less than 10 wt % based on the total weight of the adjuvant. The pre-mix composition may further comprise a viscosity modifying agent, preferably selected from the group consisting of an attapulgite, a cellulose derivative, and a combination thereof. The adjuvant may further comprise surfactant present in an amount less than 5 wt %, e.g., less than 3 wt %, based on the total weight of the adjuvant. The surfactant may have a hydrophilic lipophilic balance less than 15. The surfactant may comprise a compound selected from the group consisting of oleates, polyoxyethylene/polyoxypropylene block copolymers, alcohol ethoxylates, glycols, fatty acid esters, sulfates, sulfonates, sulfonic acids, and mixtures thereof. The plasticizer, in some cases, is selected from the group consisting of a triethylene glycol diester, a polyalkylene glycol, triethylene glycol di-2-ethylhexoate, a polyether polyol, an ester of canola oil, an ester of castor oil, 2,2,4-trimethyl-1,3-pentanediol monoisobutyrate, a phthalate, an adipic acid polyesters, a trimellitate, an adipate, an epoxy ester, a polyetherester, a benzoate, a dipropylene glycol dibenzoate, a diethylene glycol dibenzoate, epoxidized methyl ester of soy oil, methyl ester of soy oil, and mixtures thereof.

In one embodiment, the invention relates to an agricultural spray composition comprising an active ingredient and the pre-mix composition discussed above. The active ingredient may be selected from the group consisting of herbicides, pesticides, fungicides, insecticides, acaricides, nematocides, foliar nutrients, defoliants, plant growth regulators, molluscicides and mixtures thereof.

The invention, in some cases, relates to a process for treating an agricultural product, comprising spraying on the agricultural product the agricultural spray composition discussed above. The spraying may form droplets and no more than 10 vol % of the droplets may have a droplet size less than 105 µm, when sprayed using a flat fan nozzle. The agricultural spray composition may further comprise water. The agricultural spray composition may comprise at least 95 wt % water and at least 1 wt % pre-mix composition.

The invention, in some embodiments, process for producing an agricultural spray composition comprising providing an agricultural spray pre-mix composition, as discussed above, and adding to the agricultural spray a pre-mix composition an active ingredient to form the agricultural spray composition. The agricultural spray composition may comprise the active ingredient and the pre-mix composition. The active ingredient may be selected from the group consisting of herbicides, pesticides, fungicides, insecticides, acaricides, nematocides, foliar nutrients, defoliants, plant growth regulators, molluscidcides, and mixtures thereof. Preferably, the agricultural spray composition and the water conditioning agent are combined prior to the addition of the active ingredient. The water conditioning agent and the plasticizer may be as discussed above. The agricultural spray composition preferably has an efficacy of more than 50% kill rate. In some cases, the invention relates to a process for treating an agricultural product, comprising spraying on the agricultural product an agricultural spray composition, as discussed above. The spraying may form droplets and no more than 10 vol % of the droplets may have a droplet size less than 105 µm, when sprayed using a flat fan nozzle. The agricultural spray composition may further comprise water, e.g., at least 95% water and at least 1 wt % pre-mix composition.

DETAILED DESCRIPTION OF THE INVENTION

It has now been discovered that the combination of a polymer dispersion, a plasticizer, and an agriculturally active ingredient provides for an agricultural spray composition having improved properties. In some embodiments, the polymer dispersion and the plasticizer combine to form an adjuvant.

In some embodiments, the agricultural spray composition, advantageously demonstrates, inter alia, a synergistic reduction in driftable fines and/or maintenance of the relative span of droplet size as compared to agricultural spray compositions employing conventional agricultural spray adjuvants or no adjuvants at all. The vinyl ester-based polymer dispersion may be any suitable one, e.g., a stabilized polymer dispersion that may be stabilized with a protective colloid and/or a surfactant. In some embodiments, the polymer dispersion may be produced from one or more monomers, at least one of the monomers comprising a vinyl ester of a carboxylic acid and having up to 20 carbon atoms, e.g., up to 15 carbon atoms or up to 10 carbon atoms, stabilized by a protective colloid or a surfactant. Preferably the vinyl ester of a carboxylic acid comprises vinyl acetate. In one embodiment, the one or more monomers further comprise ethylene. The plasticizer preferably comprises a triethylene glycol diester, e.g., triethylene glycol di-2-ethylhexanoate ("3G8"). In some embodiments, the plasticizer has a high boiling point, e.g., greater than 110° C., greater than 150° C., or greater than 250° C. and/or a low volatility. The combination of the adjuvant (the polymer dispersion and the plasticizer) with the active ingredient provides for the improved agricultural spray composition.

Conventional compositions may comprise such a polymer dispersion and a plasticizer. These conventional compositions, however, are utilized in adhesive- and paint-related applications and are not known to be utilized in combination with an active ingredient to form an agricultural spray composition. Thus, these conventional compositions (and teachings relating thereto) are not relevant to the present adjuvant and agricultural spray composition. Importantly, in conventional applications, the polymer dispersions are present in higher concentrations, while the other components, e.g., the plasticizers, are present in lower concentrations. For example, in a conventional application, a polymer dispersion/plasticizer composition may comprise greater than 85 wt % polymer dispersion and less than 15 wt % plasticizer.

The present invention, however, utilizes the polymer dispersion and the plasticizer for entirely different applications and in entirely different proportions (in the adjuvant, in the pre-mix composition, or in the agricultural spray composition).

It has also been discovered that pre-mix concentrates comprising a polymer dispersion, plasticizer, and a water conditioning agent (and optionally other components) are beneficial for their ease of use arising from a limited number of products to mix, and reduced mixing time. The use of stable pre-mix concentrates has also been found to eliminate incompatibility issues that may be encountered in mixing individual ingredients separately. In use, the disclosed pre-mix concentrates may be advantageously combined with a diluent, e.g., water, and/or active ingredients to form the agricultural spray compositions, which are then employed in (agricultural) applications.

In particular, the combination of specific agricultural spray adjuvants and water conditioning agents has been found to show improvements in stability and dispersion in diluent, e.g., water, as well as having the aforementioned application-related benefits. In the pre-mix composition, the adjuvant and water conditioner are present in amounts higher than the typical effective use rates for the respective components.

In one embodiment, the agricultural spray pre-mix composition comprises an agricultural spray adjuvant and a water softener. The agricultural spray adjuvant, in some cases, comprises a vinyl ester-based or vinyl acrylate-based polymer dispersion and a plasticizer.

The adjuvant may be present in the pre-mix composition, in an amount ranging from 0.01 wt % to 40 wt %, based on the total weight of the pre-mix composition, e.g., from 5 wt % to 40 wt %, from 0.1 wt % to 35 wt %, or from 0.5 wt % to 30 wt %. In terms of lower limits, pre-mix composition comprises the adjuvant in an amount greater than 0.01 wt %, e.g., greater than 0.1 wt %, greater than 0.5 wt %, greater than 1 wt %, greater than 3 wt %, greater than 5 wt %, or greater than 10 wt %. In terms of upper limits, pre-mix composition comprises the adjuvant in an amount less than 40 wt %, e.g., less than 35 wt %, less than 30 wt %, less than 25 wt %, less than 20 wt %, less than 15 wt %, or less than 10 wt %.

The water conditioning agent may be present in the pre-mix composition, in an amount ranging from 1 wt % to 50 wt %, based on the total weight of the pre-mix composition, e.g., from 3 wt % to 40 wt %, from 5 wt % to 50 wt %, from 10 wt % to 35 wt %, or from 15 wt % to 25 wt %. In terms of lower limits, pre-mix composition comprises the water conditioning agent in an amount greater than 1 wt %, e.g., greater than 3 wt %, greater than 5 wt %, greater than 10 wt %, greater than 15 wt %, or greater than 20 wt %. In terms of upper limits, pre-mix composition comprises the water conditioning agent in an amount less than 50 wt %, e.g., less than 45 wt %, less than 40 wt %, less than 35 wt %, less than 30 wt %, less than 25 wt %, or less than 20 wt %. The water conditioning agent may comprise a compound selected from the group consisting of nitrogen-containing sulfates, (sulfur-containing) carboxylic acids, phosphate salts and mixtures thereof, preferably being selected from nitrogen-containing sulfates and/or sulfur-containing carboxylic acids. Other exemplary water conditioning agents include ammonium sulfates, ammonium nitrates, ammonium alkyl aryl sulfonates, ammonium polyacrylates, citrophosphates, glycerol acids, hydroxy carboxylic acids, phosphate esters, phosphoric acids, polyacrylic acids, propionic acid, sulfates, ureas, urea sulfates, and mixtures thereof.

In one embodiment, the plasticizer is present in the adjuvant in an amount from 15 wt % to 70 wt %, based on the total weight of the adjuvant, e.g., from 15 wt % to 60 wt %, from 20 wt % to 50 wt %, or from 20 wt % to 40 wt %. In terms of limits, the plasticizer may be present in an amount greater than 15 wt %, e.g., greater than 20 wt %, greater than 25, wt %, or greater than 30 wt %. The plasticizer may be present in an amount less than 70 wt %, based on the total weight of the adjuvant, e.g., less than 60 wt %, less than 50, wt %, or less than 40 wt %. Preferably, the plasticizer is selected from the group consisting of a triethylene glycol diester, a polyalkylene glycol, triethylene glycol di-2-ethylhexoate, a polyether polyol, an ester of canola oil, an ester of castor oil, 2,2,4-trimethyl-1,3-pentanediol monoisobutyrate, a phthalate, an adipic acid polyesters, a trimellitate, an adipate, an epoxy ester, a polyetherester, a benzoate, a dipropylene glycol dibenzoate, a diethylene glycol dibenzoate, epoxidized methyl ester of soy oil, methyl ester of soy oil, and a mixture of two more thereof. This listing is non-limiting. Plasticizer(s) are further discussed below.

In some embodiments, the polymer dispersion is present in the adjuvant an amount from 30 wt % to 85 wt %, based on the total weight of the adjuvant, e.g., from 35 wt % to 80 wt %, from 35 wt % to 75 wt %, or from 40 wt % to 70 wt %. In terms of limits, the polymer dispersion may be present in an amount less than 85 wt %, based on the total weight of the adjuvant, e.g., less than 80 wt %, less than 75 wt %, or less than 70 wt %. The polymer dispersion may be present in an amount greater than 35 wt %, based on the total weight of the adjuvant, e.g., greater than 40 wt %, greater than 45, wt %, or greater than 50 wt %.

The adjuvant may be utilized alone or as a component of the pre-mix composition.

The polymer dispersion is present in concentrations much lower than in typical applications, e.g., adhesives, and the plasticizer is present in amounts much higher than in typical applications.

The pre-mix composition, in some embodiments, shows a non-Newtonian rheology having a viscosity less than about 150 cp, as measured by a rotational rheometer, e.g., less than 140 cp, less than 130 cp, less than 120 cp, less than 110 cp, less than 100 cp, less than 80 cp, less than 60 cp, less than 50 cp, or less than 25 cp.

In some cases, the pre-mix composition has a pH ranging from 2 to 8, e.g., from 2.5 to 7.5, from 3 to 7, from 3.5 to 6.5, or from 4 to 6. In terms of lower limits, the pH may be greater than 2, e.g., greater than 2.5, greater than 3, greater than 3.5, greater than 4, greater than 4.5, greater than 5, greater than 5.5 or greater than 6. In terms of upper limits, the pH may be less than 8, less than 7.5, less than 7, less than 6.5, less than 6, less than 5.5, less than 5, less than 4.5, less than 4, less than 4, or less than 3.5.

In one embodiment, the concentration of plasticizer is more than 15% of the concentration of the polymer dispersion, e.g., more than 25%, more than 30%, more than 40%, more than 50%, more than 60%, more than 70%, more than 80%, or more than 90%, based on the concentration of the polymer dispersion.

In one embodiment, the pre-mix composition comprises a surfactant. Suitable surfactants are discussed herein. In some cases, the surfactant may be present in the pre-mix composition in an amount less than 15 wt % based on the total weight of the pre-mix composition, e.g., less than 12 wt %, less than 10 wt %, less than 8 wt %, less than 5 wt %, or less than 3 wt %. In terms of lower limits, the surfactant may be present in the pre-mix composition in an amount greater than 0.1 wt % based on the total weight of the pre-mix composition, e.g., greater than 1 wt %, greater than 3 wt %, greater than 5 wt %, or greater than 8 wt %. In terms of ranges, the surfactant may be present in the pre-mix composition in an amount ranging from 0.1 wt % to 15 wt %, e.g., from 1 wt % to 12 wt %, from 1 wt % to 10 wt %, or from 3 wt % to 10 wt %.

In some cases, the adjuvant comprises surfactant. The adjuvant may comprise surfactant present in an amount less than 10 wt % based on the total weight of the adjuvant, e.g., less than 8 wt %, less than 5 wt %, or less than 3 wt %. In terms of lower limits, the surfactant may be present in the adjuvant in an amount greater than 0.1 wt % based on the total weight of the pre-mix composition, e.g., greater than 1 wt %, greater than 3 wt %, or greater than 5 wt %. In terms of ranges, the surfactant may be present in the adjuvant in an amount ranging from 0.1 wt % to 10 wt %, e.g., from 0.1 wt % to 8 wt %, from 1 wt % to 8 wt %, or from 1 wt % to 5 wt %. Beneficially, because of the synergistic combination of polymer dispersion and water conditioner, smaller amounts of surfactant can be utilized to achieve effective results.

Preferably, the surfactant has a hydrophilic lipophilic balance less than 15, less than 13, less than 12, less than 10, less than 8, less than 7, less than 5, or less than 3. In one embodiment, the surfactant is selected from the group consisting of oleates, polyoxyethylene/polyoxypropylene block copolymers, glycols, fatty acid esters (such as ethoxylated fatty acid esters), sulfates, alcohol ethoxylates, sulfonates, sulfonic acids, and mixtures thereof. This listing is non-limiting. Surfactant(s) are further discussed below.

As noted above, the pre-mix compositions described herein demonstrate surprising improvements in stability, dispersion in diluent, and sprayability (as shown in the examples). For example, when combined with diluent, e.g., water, at a weight ratio of at least 95:1, the pre-mix composition may have a viscosity less than 5 cp as measured by a rotational rheometer, e.g., less than 4 cp, less than 3 cp, less than 3 cp, or less than 2 cp. As another example, after at least two weeks of storage at 25° C. the pre-mix composition shows substantially no macro separation (macro separation is discussed in the examples). Further, when mixed with water at a volume ratio of 0.05 ounces/gallon to 1 ounce/gallon and after at least two weeks of storage at 25° C., the resultant composition is a homogeneous dispersion, e.g., no particulates or solid particles are present in the resultant mixture.

In one embodiment, the adjuvant has a static surface tension from 30 dynes/cm to 60 dynes/cm, e.g., 35 dynes/cm to 55 dynes/cm or 40 dynes/cm to 50 dynes/cm. In some embodiments the adjuvant has a viscosity from 100 cp to 10000 cp, e.g., from 200 cp to 6000 cp for from 500 cp to 4000 cp. In some embodiments, the pH of the adjuvant and/or an adjuvant concentrate may be between 3.0 to 8.5, e.g., from 3.5 to 7, or from 4 to 6.

The invention also relates to a method for producing a spray adjuvant. The method comprises the steps of providing the vinyl ester-based polymer dispersion and adding a plasticizer to the vinyl ester-based polymer dispersion. Preferably, the greater than 15 wt % of plasticizer, is added to the polymer dispersion.

Plasticizer

The combination of plasticizer and polymer dispersion surprisingly yields an adjuvant composition having synergistic properties and characteristics. In some cases, the use of specific concentrations of plasticizer and polymer dispersion contributes to the synergistic properties and characteristics. It is believed that the synergy comes from the combination being able to reduce driftable fines using both mechanisms. In some embodiments, without being bound by theory, it is believed that most of the plasticizer (in the adjuvant) is able to preferentially enter into the polymer colloid of the aqueous polymer dispersion with the rest likely present in the water phase as emulsified droplets. The plasticizer in the polymer phase is believed to interpose between the individual strands of polymers thereby causing breakdown of polymer-polymer interactions. This beneficially makes the polymer more porous and flexible, and makes its structure less cohesive. Plasticizers having polarity that is similar to the polymer but different from water may also soften and swell the polymer colloid (latex colloids), which aids in overcoming resistance to deformation. As a result, the plasticized aqueous polymer dispersion deforms at a lower tensile force as compared to without plasticizer. This effect in turn enhances the film elongation effect. The plasticizers are also known to decrease the surface tension at the polymer surface. In effect, it is postulated that the polymer phase acts as a carrier for the plasticizer. The resulting adjuvant is essentially a single phase and may be easily mixed in an agricultural spray composition with minimal mixing, unlike conventional oil based adjuvants, which are typically immiscible with water. The single phase nature of the inventive adjuvant composition allows it to be used in crop protection sprays with minimal or no use of surfactants. In addition to the ability to alter the physical and mechanical properties of the polymers of the aqueous polymer dispersion, the plasticizers may be able to diffuse out of the polymer to beneficially aid in adhesion and spreading on the leaf surface.

Further, because of the high boiling points of the plasticizers and because the fact that most of the plasticizer is occluded in the polymer colloid and not readily exposed to environment, the plasticizers can advantageously keep the sprayed droplets wet for a longer period of time, which allows more time for the active ingredient(s) to diffuse through the leaf cuticle and be absorbed by the plant.

In some cases, efficient plasticizers generally meet a basic requirement, namely, that all the intermolecular forces involved (between plasticizer and plasticizer, between polymer and polymer, between plasticizer and polymer) are of the same order of magnitude. The thermodynamic basis for such interactions is expressed by Hildebrand solubility parameters, defined as the square root of cohesive energy density. Plasticizer compatibility with an amorphous polymer such as the polymer dispersions used in this invention, $\delta$, normally requires values that do not differ by more than ±1.5 (cal./cc). Solubility parameters for both polymers and plasticizers are conveniently calculated by the additive method of Small, who has derived individual parameters for various atoms and groups in the molecules. Compilations of molar attraction constants, commonly known as Small's constants, are given in many references, e.g., "The Function and Selection of Ester Plasticizers," Hallstar Technical Publication, O'Brien, J. L., "Plasticizers", in Modern Plastics Encyclopedia, McGraw Hill, New York, 1988, p. 168., Polymer/Plasticizer Polarity Chart (brochure), The C. P. Hall Company, 311 S. Wacker, Chicago, Ill. 60606)

In addition to the balance of intermolecular forces, efficient plasticizers show low volatility, high solvent power, compatibility with polymer, similar polarity to the polymer, and temperature stability. These properties control the how fast the plasticizer can diffuse in and out of the polymer and it ability to interpose between the polymer chains. The choice of a plasticizer, therefore, usually involves a compromise since the requirements for good solvent power, compatibility, efficiency, and permanence, cannot all be met simultaneously all the time. (Principles of Plasticization, Edmund H. Immergut and Herman F. Mark, Polytechnic Institute of Brooklyn, Brooklyn, N.Y., Chapter 1, http://pubs.acs.org. In one embodiment, the plasticizer is a particular plasticizer selected from the group consisting of a triethylene glycol diester, e.g., triethylene glycol di-2-ethylhexoate ("3G8"), polyalkylene glycols, polyether polyols, esters of canola oil, esters of castor oil, 2,2,4-trimethyl-1,3-pentanediol monoisobutyrate, phthalates, non-phthalates (adipic acid polyesters, trimellitates, adipates, epoxy esters, polyetheresters, benzoates, dipropylene glycol dibenzoate, diethylene glycol dibenzoate), epoxidized methyl ester of soy oil, methyl ester of soy oil, and mixtures thereof. The plasticizer preferably comprises a triethylene glycol diester, e.g., triethylene glycol di-2-ethylhexoate ("3G8"). In one embodiment, the plasticizer does not include propylene glycol and/or glycol ethers. Generally speaking, these plasticizers have a unique combination of properties that leads to the surprising adjuvant compositions discussed herein, e.g., the plasticizers are hydrophobic, immiscible with water, have high boiling points, and/or show good plasticizer response. In an embodiment, the plasticizer response ranges from 0.5 to 15, e.g., from 1.2 to 8.

Plasticizer response may be measured as follows: measuring the initial viscosity of 200 grams of the polymer dispersion, e.g., using a Brookfield Viscometer, RV, Spindle #5, 20 rpm; stirring the polymer dispersion, e.g., at 500 rpm, and adding 50 grams of plasticizer, e.g., over 10 minutes (stirring speed may be increased to insure good mixing; the blend may be further stirred, e.g., for 15 minutes, once all the plasticizer is added); remeasuring the viscosity of the blend, e.g., at 1 hour and then at 24 hours; and calculating the plasticizer response as the ratio of final viscosity of the blend at 24 hours to the original viscosity of the neat polymer without the plasticizer.

Suitable commercial plasticizers include, but are not limited to, Celvaset™ PL-1000, Soygold® 2500, Optifilm™ Enhancer 400, Steposol® SBD; Loxanol® EFC 300, Lusolvan® FBH, Pluriol® WS 600, ADM CA 118, Pluracoat™ CA 100, Pluracoat™ CA 110, Pluracoat™ CA 120, OxiCure® 2000, Soyanol SGE 40, Texanol™, and Benzoflex™ 50.

The adjuvant may further comprise a viscosity modifying agent. In some embodiments, the viscosity modifying agent is selected from the group consisting of polyvinyl alcohol, polyethylene oxides, polyethylene glycols, polypropylene glycols, cellulose derivatives, starches, attapulgites, synthetic clays, fumed silica, colloidal silica, hydrogenated castor wax, polyamide, carboxy functional acrylic, associative thickeners, alkali-swellable emulsions, alkali soluble emulsions, hydrophobically modified alkali-swellable emulsions, hydrophobically modified ethoxylated urethane resins, and mixtures thereof Polymer Dispersion The polymer dispersion may vary widely and will be produced from one or more monomers. The monomer(s) preferably comprise a vinyl ester of a carboxylic acid and having up to 20 carbon atoms, e.g., up to 15 carbon atoms or up to 10 carbon atoms.

The aqueous polymerization mixture can be substantially free of seed polymer particles, by which is meant that that the mixture contains less than 5 wt %, preferably less than 1 wt % and most preferably no added seed polymer particles.

Monomers

The (aqueous) polymerization mixture used to produce the present polymer dispersion comprises one or more free-radically polymerizable main monomers. Suitable main monomers are selected from $C_1$-$C_{20}$-alkyl (meth)acrylates, vinyl esters of carboxylic acids with up to 20 carbons, vinyl-aromatic compounds having up to 20 carbons, ethylenically unsaturated nitriles, vinyl halides, vinyl ethers of $C_1$-$C_{10}$ alcohols, $C_2$-$C_8$ aliphatic hydrocarbons with 1 or 2 double bonds, and mixtures of these monomers. In one embodiment, the polymer dispersion comprises monomers comprising a vinyl ester of a carboxylic acid.

Preferred alkyl (meth)acrylates are $C_1$-$C_{10}$-alkyl (meth) acrylates, such as methyl methacrylate, methyl acrylate, n-butyl acrylate, ethyl acrylate and 2-ethylhexyl acrylate. Mixtures of alkyl (meth)acrylates can also be employed.

Examples of suitable vinyl esters of $C_1$-$C_{20}$ carboxylic acids include vinyl acetate, vinyl propionate, vinyl laurate, vinyl stearate, vinyl benzoate, vinyl 2-ethyl hexanoate and Versatic acid vinyl esters. Preferably the vinyl ester of a carboxylic acid comprises vinyl acetate.

Suitable vinyl-aromatic compounds include vinyltoluene, α- and p-methylstyrene, α-butylstyrene, 4-n-butylstyrene, 4-n-decyl-styrene and, preferably, styrene.

Examples of suitable nitriles include acrylonitrile and methacrylonitrile.

Suitable vinyl halides include chloro-, fluoro- or bromo-substituted ethylenically unsaturated compounds, such as vinyl chloride and vinylidene chloride.

Examples of vinyl ethers are vinyl methyl ether and vinyl iso-butyl ether, with preference being given to vinyl ethers of $C_1$-$C_4$ alcohols.

Examples of suitable $C_2$-$C_8$ aliphatic hydrocarbons with one olefinic double bond include ethene and propene, whereas representative examples of $C_2$-$C_8$ aliphatic hydrocarbons having two olefinic double bonds include butadiene, isoprene and chloroprene.

In one embodiment, the present polymer dispersion is produced from a mixture of free-radically polymerizable main monomers comprising from 50 wt % to 99 wt % vinyl acetate and from 1 wt % to 40 wt % ethylene.

Co-Monomers

In addition to the main monomers discussed above, the aqueous polymerization mixture used to produce the present polymer dispersion may comprise up to 10 wt % of auxiliary co-monomer(s) based on the total weight of monomers in the mixture. Such auxiliary co-monomers can be those which promote better film or coating performance by the compositions herein or can provide films and coatings of desirable properties. Such desirable properties can include, for example, enhanced adhesion to low surface energy surfaces or substrates, less rebound on impacting a surface, improved spreading on waxy surfaces, longer open time, and improved resistance to film or coating drying and cracking. The optional co-monomers useful for incorporation into the emulsion copolymers of the compositions herein are those which contain at least one polymerizable double bond along with one or more additional functional moieties. Preferably, the co-monomers comprise ethylenically unsaturated monomers capable of polymerizing with the vinyl ester. Suitable auxiliary co-monomers include unsaturated organic acids, unsaturated silanes, glycidyl co-monomers, ureido co-monomers, co-monomers with crosslinkable functions, crosslinking co-monomers and combinations thereof.

Suitable auxiliary co-monomers including unsaturated organic acids comprise ethylenically unsaturated carboxylic acids and anhydrides and amides thereof, ethylenically unsaturated sulfonic acids, and ethylenically unsaturated phosphonic acids.

For example, the auxiliary monomer may comprise an ethylenically unsaturated $C_3$-$C_8$ monocarboxylic acid and/or an ethylenically unsaturated $C_4$-$C_8$ dicarboxylic acid, together with the anhydrides or amides thereof. Examples of suitable ethylenically unsaturated $C_3$-$C_8$ monocarboxylic acids include acrylic acid, methacrylic acid and crotonic acid. Examples of suitable ethylenically unsaturated $C_4$-$C_8$ dicarboxylic acids include maleic acid, fumaric acid, itaconic acid and citraconic acid.

Examples of suitable ethylenically unsaturated sulfonic acids include those having 2-8 carbon atoms, such as vinylsulfonic acid, 2-acrylamido-2-methylpropanesulfonic acid, 2-acryloyloxyethanesulfonic acid and 2-methacryloyloxyethanesulfonic acid, 2-acryloyloxy- and 3-methacryloyloxy-propanesulfonic acid. Examples of suitable ethylenically unsaturated phosphonic acids also include those having 2-8 carbon atoms, such as vinylphosphonic acid and ethylenically unsaturated polyethoxyalkyletherphosphates.

In addition to or instead of said acids, it is also possible to use the salts thereof, preferably the alkali metal or ammonium salts thereof, particularly preferably the sodium salts thereof, such as, for example, the sodium salts of vinylsulfonic acid and of 2-acrylamidopropanesulfonic acid.

Unsaturated silanes useful as auxiliary co-monomers can generally correspond to the structural Formula I:

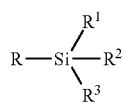

Formula I in which R denotes an organic radical olefinically unsaturated in the ω-position and $R^1$, $R^2$ and $R^3$ which may be identical or different, denote the group —OZ, Z denoting hydrogen or primary or secondary alkyl or acyl radicals optionally substituted by alkoxy groups. Suitable unsaturated silane compounds of the Formula I are preferably those in which the radical R in the formula represents an ω-unsaturated alkenyl of 2 to 10 carbon atoms, particularly of 2 to 4 carbon atoms, or an ω-unsaturated carboxylic acid ester formed from unsaturated carboxylic acids of up to 4 carbon atoms and alcohols carrying the Si group of up to 6 carbon atoms. Suitable radicals $R^1$, $R^2$, $R^3$ are preferably the group —OZ, Z representing primary and/or secondary alkyl radicals of up to 10 carbon atoms, preferably up to 4 carbon atoms, or alkyl radicals substituted by alkoxy groups, preferably of up to 3 carbon atoms, or acyl radicals of up to 6 carbon atoms, preferably of up to 3 carbon atoms, or hydrogen. Most preferred unsaturated silane co-monomers are vinyl trialkoxy silanes.

Examples of preferred silane compounds of the Formula I include γ-methacryloxypropyltris(2-methoxyethoxy)silane, vinylmethoxysilane, vinyltriethoxysilane, vinyldiethoxysilanol, vinylethoxysilanediol, allyltriethoxysilane, vinyltripropoxysilane, vinyltriisopropoxysilane, vinyltributoxysilane, vinyltriacetoxysilane, trimethylglycolvinylsilane, γ-methacryloxypropyltrimethylglycolsilane, γ-acryloxypropyltriethoxysilane and γ-methacryloxypropyltrimethoxysilane.

Glycidyl compounds can also be used as optional auxiliary co-monomers to impart epoxy-functionality to the emulsion copolymer. Examples of suitable glycidyl optional co-monomers include glycidyl acrylate, glycidyl methacrylate, allyl glycidyl ether, and vinyl glycidyl ether.

Another type of optional co-monomer comprises cyclic ureido co-monomers. Cyclic ureido co-monomers are known to impart improved wet adhesion properties to films and coatings formed from copolymers containing these co-monomers. Cyclic ureido compounds and their use as wet adhesion promoting co-monomers are disclosed in U.S. Pat. Nos. 4,104,220; 4,111,877; 4,219,454; 4,319,032; 4,599,417 and 5,208,285. The disclosures of all of these U.S. patents are incorporated herein by reference in their entirety.

Another type of optional co-monomer comprises co-monomers with crosslinkable functions such as N-methylolacrylamide, N-methylolmethacrylamide, N-methylolallylcarbamate, N-methylolmaleimide, N-methylolmaleamic acid, and the N-methylol amides of aromatic vinyl carboxylic acids, such as N-methylol-p-vinylbenzamide. N-ethanol (meth)acrylamide, N-propanol(meth)acrylamide, the N-methylol esters or N-alkyl ethers or Mannich bases of N-methylol(meth)acrylamide or N-methylolallylcarbamate, acrylamidoglycolic acid and/or its salts, methyl acrylamidomethoxyacetate or N-(2,2-dimethoxy-1-hydroxyethyl) acrylamide.

A further group of comonomers suitable for preparing the emulsion polymers used herein comprises crosslinking monomers, such as comonomers with polyethylenic unsaturation, and hence with a crosslinking action. Examples include diallyl phthalate, diallyl maleate, triallyl cyanurate, tetraallyloxyethane, divinylbenzene, butane-1,4-diol dimethacrylate, triethylene glycol dimethacrylate, divinyl adipate, allyl (meth)acrylate, vinyl crotonate, methylenebisacrylamide, hexanediol diacrylate, pentaerythritol diacrylate and trimethylolpropane triacrylate.

Stabilizers

The polymer dispersion, in some embodiments, may be a stabilized polymer dispersion. The stabilized polymer dispersion may be stabilized by a suitable stabilizer, e.g., a protective colloid, a surfactant, or a mixture thereof. Generally, the stabilizer composition comprises one or more stabilizers selected from protective colloids, anionic and/or non-ionic surfactants and mixtures thereof. Generally, the stabilizer(s) are present in the aqueous polymerization mixture in an amount between 0.5 wt % and 15 wt %, e.g., between 1 wt % and 12 wt % or between 2 wt % and 10 wt %, by weight based on the total weight of monomer(s) in the polymer dispersion. In terms of upper limits, the stabilizer may be present in an amount less than 15 wt %, e.g., less than 12 wt % or less than 10 wt %. In terms of lower limits, the stabilizer may be present in an amount greater than 0.5 wt %, e.g., greater than 1 wt % or greater than 2 wt %.

In one embodiment, the polymer dispersion is stabilized by a protective colloid, and the protective colloid may vary widely. Suitable protective colloids for use as one or more of the further stabilizer(s) include polyvinyl alcohols, polyvinyl pyrrolidone, methylcelluloses, hydroxyethyl- and propylcelluloses, and also sodium carboxymethylcellulose, gelatin, casein, starch, gum arabic, hydroxy ethyl starch and sodium alginate. Suitable polyvinyl alcohols for use as a further stabilizer are substantially free of acid groups and have a molar degree of hydrolysis of at least 86. These standard grade polyvinyl alcohols have Höppler viscosities which are chosen to match the desired end viscosity of the dispersion. Conveniently these standard grades comprise a mixture of at least two polyvinyl alcohols to adjust the viscosity of the polymer dispersion. In one embodiment, the at least one further stabilizer comprises a polyvinyl alcohol having a lower Höppler viscosity value for example in a 4 weight % aqueous solution at 20° C. of 4.8 to 5.8 mPa·s and a further polyvinyl alcohol having a higher Höppler viscosity value for example in a 4 weight % aqueous solution at 20° C. of 27 to 33 mPa·s.

In some embodiments, the protective colloid is selected from the group consisting of hydroxyl ethyl cellulose, polyvinyl alcohol, polyethylene oxide, starch, and mixtures thereof. Generally speaking, a protective colloid is a compound or composition that stabilizes the polymer. In some cases the protective colloid is disposed on the surface of the polymer(s) and coats the polymer(s), which results in stabilization. Preferably, the protective colloid comprises hydroxyl ethyl cellulose.

In some cases where the polymer dispersion is stabilized by a protective colloid, the dispersion and/or the adjuvant as a whole, may contain little if any surfactant emulsifier, e.g., the dispersion and or the adjuvant is substantially surfactant free, e.g., less than 0.1 wt %, less than 0.05 wt %, less than 0.03 wt %, or less than 0.01 wt % surfactant. Without being bound by theory, it is believed that the low surfactant content beneficially results in the reduction of driftable fines. A water molecule within the bulk of water experiences attractions to neighboring water molecules in all directions. But since these attractions average out to zero, there is no net force on the water molecule. However, the water molecules at the surface of a quantity of water are subject to unequal forces. Typically, a smaller surface area usually lowers the overall potential energy thereof. Thus intermolecular attractive forces act to minimize the surface area of a liquid. The geometric shape that has the smallest ratio of surface area to volume is the sphere, so very small quantities of liquids tend to form spherical drops. There is a change in pressure across a curved surface or interface such as a sphere. The pressure change is represented by Young-Laplace equation, as shown in Formula I below, where $\Delta P$ is the Laplace pressure, R is the radius of curvature of the surface, $\eta$ is the surface tension. A smaller droplet size (smaller radius) has greater internal pressure. Hence the pressure in a smaller bubble would be much higher in comparison to the pressure inside a larger bubble, which would make the bubbles inherently unstable, e.g., the bubbles would burst. It is postulated that surfactants reduce the surface tension of water, e.g., by a factor of 3 or more, thus reducing the internal pressure and making the smaller water droplets more stable. Accordingly, it is believed that highly surfactant-loaded crop protection sprays can generate significant amount of driftable fines by stabilizing these small droplets.

$$\Delta P = P_{inside} - P_{outside} = (4\eta)/R \qquad \text{Formula I}$$

In some cases, the dispersion and/or the adjuvant as a whole, may contain little if any protective colloid stabilizer, e.g., the dispersion and or the adjuvant is substantially protective colloid free, e.g., the stabilizing system comprises less than 1.0 pphm of protective colloid, less than 0.5 pphm protective colloid, or less than 0.1 pphm protective colloid. (see US patent 20140162018, section 0013

In some embodiments, the polymer dispersion is stabilized with a surfactant emulsifier, and the surfactant emulsifier may vary widely. In some embodiments, the surfactant emulsifier is selected from the group consisting of one or more anionic and nonionic surfactant emulsifiers. Amphoteric and/or polymerizable surfactants may also be employed, alone or in combination with the anionic and/or nonionic surfactants.

The nonionic surfactant emulsifiers may vary widely. Some exemplary nonionic surfactant emulsifiers include, but are not limited to, polyoxyethylene condensates, e.g., polyoxyethylene aliphatic ethers, such as polyoxyethylene lauryl ether and polyoxyethylene oleyl ether; polyoxyethylene alkaryl ethers, such as polyoxyethylene nonylphenol ether and polyoxyethylene octylphenol ether; polyoxyethylene esters of higher fatty acids, such as polyoxyethylene laurate and polyoxyethylene oleate; condensates of ethylene oxide with resin acids and tall oil acids; polyoxyethylene amide; amine condensates such as N-polyoxyethylene lauramide, and N-lauryl-N-polyoxyethylene amine; and polyoxyethylene thio-ethers such as polyoxyethylene n-dodecyl thio-ether. In a preferred embodiment, the surfactant is sodium dioctyl sulfosuccinate, e.g., Aerosol® OT-75 PG.

Other suitable nonionic surfactant emulsifiers include, but are not limited to, a series of surface active agents available from BASF under the Pluronic® and Tetronic® trade names. Some Pluronic surfactants are ethylene oxide (EO)/Propylene oxide (PO)/ethylene oxide block copolymers that are prepared by the controlled addition of PO to the two hydroxyl groups of propylene glycol. EO is then added to sandwich the hydrophobe between two hydrophilic groups. The preparation methods may be controlled such that the length constitutes from 10% to 80% (w/w) of the final molecule. Other Pluronic surfactants are PO/EO/PO block copolymers prepared by adding EO to ethylene glycol to provide a hydrophile of designated molecular weight. PO is then added to obtain hydrophobic blocks on the outside of the molecule. Exemplary Tetronic surfactants are tetrafunctional block copolymers derived from the sequential addition of PO and EO to ethylene-diamine. Other Tetronic surfactants may be produced by the sequential addition of EO and PO to ethylene-diamine.

Other suitable nonionic surfactants include, but are not limited to, a series of ethylene oxide adducts of acetyleneic glycols, sold commercially by Air Products under the Surfynol™ trade name.

Additional suitable nonionic surfactants include acyl, alkyl, oleyl and alkylaryl ethoxylates. Examples include ethoxylated mono-, di- and trialkylphenols (EO: from 3 to 50, alkyl substituted radical: $C_4$ to $C_{12}$) and ethoxylated fatty alcohols (EO: from 3 to 80; alkyl radical: $C_8$ to $C_{36}$), especially $C_{12}$-$C_{14}$-fatty alcohol ethoxylates, $C_{13}$-$C_{15}$-oxo alcohol ethoxylates, $C_{16}$-$C_{18}$-fatty alcohol ethoxylates, $C_{1-10}$-oxo alcohol ethoxylates, $C_{1-3}$-oxo alcohol ethoxylates, polyoxyethylene sorbitanmonooleate with ethylene oxide groups, copolymers of ethylene oxide and propylene oxide with a minimum content of 10% by weight of ethylene oxide, the polyethylene oxide ethers of oleyl alcohol and the polyethylene oxide ethers of nonylphenol. Particularly suitable are the polyethylene oxide ethers of fatty alcohols, especially those of $C_{12}$-$C_{14}$-fatty alcohols.

Exemplary anionic surfactants include, but are not limited to, alkyl aryl sulfonates, alkali metal alkyl sulfates, sulfonated alkyl esters and fatty acid soaps-specific examples include sodium dodecylbenzene sulfonate, sodium butylnaphthalene sulfonate, sodium lauryl sulfate, disodium dodecyl diphenyl ether disulfonate, N-octadecyl sulfosuccinate and dioctyl sodiumsulfosuccinate.

Additional suitable anionic surfactant emulsifiers include sodium, potassium and ammonium salts of straight-chain aliphatic carboxylic acids of chain length $C_{12}$-$C_{20}$, sodium hydroxyoctadecanesulfonate, sodium, potassium and ammonium salts of hydroxy fatty acids of chain length $C_{12}$-$C_{20}$ and their sulfation and/or acetylation products thereof, alkyl sulfates, also in the form of triethanolamine salts, alkyl-($C_{10}$-$C_{20}$)-sulfonates, alkyl($C_{10}$-$C_{20}$)-arylsulfonates, dimethyldialkyl-($C_8$-$C_{18}$)-ammonium chloride, and sulfation products thereof, alkali metal salts of sulfosuccinic esters with aliphatic saturated monohydric alcohols of chain length $C_4$-$C_{16}$, sulfosuccinic 4-esters with polyethylene glycol ethers of monohydric aliphatic alcohols of chain length $C_{10}$-$C_{12}$ (disodium salt), sulfosuccinic 4-esters with polyethylene glycol nonylphenyl ether (disodium salt), sulfosuccinic acid biscyclohexyl ester (sodium salt), lignosulfonic acid and the calcium, magnesium, sodium and ammonium salts thereof, resin acids, hydrogenated and dehydrogenated resin acids and alkali metal salts thereof, sodium (dodecylated diphenyl ether) disulfonate and sodium laurylsulfate, or ethoxylated sodium lauryl ether sulfate. It is also possible to use mixtures of ionic surfactant emulsifiers. Additional amphoterica and/or polymerizable surfactants are disclosed in U.S. Pat. Nos. 5,064,888 and 5,530,056)

Polymerization Process

The desired polymer dispersion may be produced by free radical emulsion polymerization of the aqueous polymerization mixture described herein in the presence of one or more free radical initiators.

A preferred free radical initiator which is used in the beginning of the polymerization is a redox initiator system comprising an oxidizing agent having a water solubility less than or equal to 15 weight %, since these are found to produce polymer dispersions with less agglomeration of the polymer particles and hence lower viscosity of the final polymer dispersion, as well as particles of more spherical shape. Examples of such oxidizing agents include organic peroxides, such as benzoyl peroxide, lauryl peroxide, t-butyl peroxide, azoisobutyronitrile and t-butyl hydroperoxide. The preferred oxidizing agent is t-butyl hydroperoxide. Alkali metal salts of oxymethanesulfinic acid, hydroxylamine salts, sodium dialkyldithiocarbamate, sodium bisulfite, ammonium bisulfite, sodium dithionite, diisopropyl xanthogen disulfide, ascorbic acid, tartaric acid, and isoascorbic acid can be used as reducing agents.

Typically, each of the oxidizing agent and the reducing agent is charged to the reaction mixture prior to polymerization in an amount from about 0.01% to about 1.0%, preferably from about 0.02% to about 0.5%, more preferably from about 0.025% to about 0.2%, by weight based on total weight of co-monomers. Generally, the molar ratio of oxidizing agent to reducing agent in the redox initiator system is from 10:1 to 1:10.

The redox initiator system used herein can also optionally comprise catalyzing metal salts of iron, copper, manganese, silver, platinum, vanadium, nickel, chromium, palladium, or cobalt. These catalyzing salts may be used at levels of from about 0.1 to about 100 ppm, with or without metal complexing agents. Preferably iron or cobalt are used.

The polymerization may be carried out in one, two or more stages using any known polymerization reactor system, such as a batch, loop, continuous, or cascade reactor system.

The polymerization temperature generally ranges from about 20° C. to about 150° C., more preferably from about 50° C. to about 120° C. The polymerization generally takes place under either atmospheric or high pressure if appropriate, preferably from about 2 to about 150 bar, more preferably from about 5 to about 100 bar. Polymers used in this invention may also be made efficiently in low pressure polymerizations of vinyl acetate polymers, e.g., pressures lower than 250 psi. The reaction is desirably performed at pressures less than 100 psi, less than 50 psi, and more preferably at substantially atmospheric pressure, that is 14.7 psi+/−10 psi.

In a typical polymerization procedure involving, for example, vinyl acetate copolymer dispersions, the vinyl acetate, stabilizing system and any other co-monomers can be polymerized in an aqueous medium under pressures up to about 120 bar in the presence the specified stabilizers and initiators. Atmospheric pressure polymerization is preferable for both batch and continuous reactors. The aqueous reaction mixture in the polymerization vessel can be maintained by a suitable buffering agent at a pH of about 2 to about 7.

The manner of combining the several polymerization ingredients, i.e., stabilizing system, co-monomers, initiator system components, etc., can vary widely. Generally an aqueous medium containing at least part of the stabilizing system can be initially formed in a polymerization vessel with the various other polymerization ingredients being added to the vessel thereafter.

Co-monomers can be added to the polymerization vessel continuously, incrementally or as a single charge addition of the entire amounts of co-monomers to be used. Co-monomers can be employed as pure monomers or can be used in the form of a pre-mixed emulsion. When present, ethylene as a co-monomer can be pumped into the polymerization vessel and maintained under appropriate pressure therein.

It is possible for the total amount of redox initiator system to be included in the initial charge to the reactor at the beginning of the polymerization. Preferably, however, a portion of the initiator is included in the initial charge at the beginning, and the remainder is added after the polymerization has been initiated, in one or more steps or continuously. In a preferred embodiment a first redox initiator system is used in the initial charge at the beginning of the polymerization comprising an oxidizing agent having a water solubility less than or equal to 15 weight %, The reaction is then continued by a second initiator system which can be the same or different from the first redox initiator system. The second initiator system can be a redox initiator system or a thermal initiator system. In a preferred embodiment the reaction is continued by means of a different initiator system which can be a thermal initiator system comprising an oxidizing agent having a water solublity of greater than 15 weight %. Examples for such oxidizing agents are hydrogen peroxide, ammonium-sodium- or potassium persulfates, peroxidisulfates or water soluble azoamidines.

As mentioned previously, the present polymerization process is normally conducted without the use of a seed latex.

On completion of the polymerization, a further, preferably chemical after treatment, especially with redox catalysts, for example combinations of the abovementioned oxidizing agents and reducing agents, may follow to reduce the level of residual unreacted monomer on the product. In addition, residual monomer can be removed in known manner, for example by physical demonomerization, i.e. distillative removal, especially by means of steam distillation, or by stripping with an inert gas. A particularly efficient combination is one of physical and chemical methods, which permits lowering of the residual monomers to very low contents (<1000 ppm, preferably <100 ppm).

Agricultural Spray Composition

As noted above, in addition to the inventive adjuvant, the present invention relates to an agricultural spray composition. The agricultural spray composition comprises the agricultural spray adjuvant discussed herein, as well as an active ingredient (and optionally a liquid carrier/diluent, e.g., water). The agricultural spray composition may further comprise optional components such as activator surfactants, leaf wetters, defoamers, and water softeners, e.g., ammonium sulfate. This listing is merely exemplary and other optional components are also contemplated.

In some embodiments, the agricultural spray composition comprising an active ingredient and the pre-mix composition discussed herein, e.g., the pre-mix composition comprising the adjuvant and the water conditioning agent. In cases where the pre-mix composition is employed, the agricultural spray composition may be produced by a process comprising providing the agricultural spray pre-mix composition and adding to the agricultural spray pre-mix composition an active ingredient to form the agricultural spray composition. Preferably, the adjuvant and the water conditioning agent are combined prior to the addition of the active ingredient.

In cases where the pre-mix composition is employed, the active ingredient may be present in an amount from 20 wt % to 99 wt %, e.g., from 30 wt % to 95 wt %, from 50 wt % to 95 wt %, or from 40 wt % to 85 wt %. In terms of upper limits, the active ingredient may be present in an amount less than 99 wt %, e.g., less than 95 wt %, less than 90, wt %, or less than 85 wt %. In terms of lower limits, the active ingredient may be present in an amount greater than 20 wt %, e.g., greater than 30 wt %, greater than 40 wt %, or greater than 50 wt %.

The adjuvant may be present in an amount from 0.1 wt % to 40 wt %, e.g., from 1 wt % to 30 wt %, from 1 wt % to 20 wt %, or from 5 wt % to 15 wt %. In terms of upper limits, the adjuvant may be present in an amount less than 40 wt %, e.g., less than 30 wt %, less than 20, wt %, or less than 15 wt %. In terms of lower limits, the adjuvant may be present in an amount greater than 0.1 wt %, e.g., greater than 1 wt %, or greater than 5 wt %.

The invention also relates to a process for treating an agricultural product. The process may comprise the steps of spraying on the agricultural product the agricultural spray composition mentioned herein. In some embodiments, the agricultural spray composition has a high efficacy, e.g., a kill rate of more than 50%, e.g., more than 60%, more than 75%, more than 85%, or more than 90%. Kill rate may be defined as the number target items, e.g., agricultural products, that are killed due to application of the agricultural spray composition, after a defined time period (for example 7, 14, or 28 days), based on the total number of target items.

Beneficially, the use of the adjuvants/pre-mix compositions/agricultural spray compositions provides for a reduction in driftable fines. In one embodiment, the spraying step forms droplets and less than 10 vol % of the droplets, e.g., less than 8 vol %, less than 5 vol %, or less than 3 vol %, have a droplet size less than 105 μm, e.g., less than 100 μm, less than 90 μm, less than 80 μm, or less than 75 μm, when sprayed using an appropriate nozzle, e.g., a flat fan nozzle. In terms of ranges, from 0.1 vol % to 10 vol %, e.g., from 1 vol % to 8 vol %, or from 5 vol % to 10 vol % of the droplets have a droplet size less than 105 μm, e.g., less than 100 μm, less than 90 μm, less than 80 μm, or less than 75 μm, when sprayed using an appropriate nozzle, e.g., a flat fan nozzle. Exemplary nozzle types in crop protection sprays are Flat Fan nozzles (XR11003 reference nozzle), air induction nozzles (AIXR11004) and turbo Teejet nozzles (TT11004). Often, types of nozzles to use are decided based on the label recommendations of the active ingredients and the desired droplet size. A more extensive information on different nozzle types and their influence on spray droplet size and spray quality are provided in the following references: "Nozzle Types for Boom Sprayer Applications of Crop Protection Products;" Robert E. Wolf, Extension Agricultural Engineer, Kansas State University, Dennis R. Gardisser, Extension Agricultural Engineer, University of Arkansas, John Slocombe, Extension Agricultural Engineer, Kansas State University, Bryan W. Shaw, Extension Agricultural Engineer, Texas A & M University Kansas State University Agricultural Experiment Station and Cooperative Extension Service, MF-2541, April 2002; and "Spray Analysis and Research Services," Rudolf J. Schick, Bulletin No. 459B.

The active ingredient may vary widely, and many active ingredients are known in the art. Active ingredients are compounds that are known to have an effect on the substrate to which the active ingredient is applied. Generally speaking, an active ingredient, e.g., an agriculturally active ingredient, is a substance (present in a pesticide composition) that is biologically active. As one explanation, according to EPA, the term "active ingredient" has been defined in FIFRA as a compound that prevents, destroys, repels or mitigates a pest. More than one active ingredient may be present. In one embodiment, the active ingredient is selected form the group consisting of herbicides, pesticides, fungicides, insecticides, acaricides, nematocides, foliar nutrients, defoliants, plant growth regulators, molluscidcides. In one embodiment, the active ingredient is selected from the group consisting of 2,4-D Dichlorophenoxyacetic acid (2,4-D), glyphosate, dicamba, triclopyr, imazapyr, sulfometuron, methyl, fluridone, clopyralid, picloram, hexazinone, chlorpyriphos, carbaryl, methomyl, ethepon, fosamine, benomyl, ferbam, zineb. In a preferred embodiment, the active ingredient is selected from the group consisting of glyphosate, 2,4-D, dicamba and mixtures thereof.

The liquid carrier may vary widely. Many liquid carriers are known in the art. Suitable liquid carriers include water, synthetic and vegetable oils. Preferably, the liquid carrier comprises water.

In some embodiments, the active ingredient is present in an amount from 0.5 wt % to 5 wt %, e.g., from 0.5 wt % to 4 wt %, from 1 wt % to 4 wt %, or from 1 wt % to 3 wt %. In terms of upper limits, the active ingredient may be present in an amount less than 5 wt %, e.g., less than 4 wt %, less than 3, wt %, or less than 2 wt %. In terms of lower limits, the active ingredient may be present in an amount greater than 0.5 wt %, e.g., greater than 1 wt %, greater than 2 wt %, or greater than 3 wt %. As noted above, the agricultural spray composition may comprise multiple active ingredients. The ranges and limits listed above apply to individual active ingredients or to combinations of the individual active ingredients.

The adjuvant may be present in an amount from 0.01 wt % to 15 wt %, e.g., from 0.01 wt % to 10 wt %, from 0.01 wt % to 5 wt %, from 0.01 wt % to 1.5 wt %, from 0.02 wt % to 2 wt %, or from 0.05 wt % to 1.5 wt %. In terms of limits, the adjuvant may be present in an amount less than 15 wt %, e.g., less than 10 wt %, less than 5 wt %, less than 1.5 wt %, less than 1, wt %, or less than 0.5 wt %. The adjuvant may be present in an amount greater than 0.01 wt %, e.g., greater than 0.02 wt %, greater than 0.05, wt %, or greater than 1 wt %. Weight percentage ranges and limits are based on the total weight of the agricultural spray composition.

In cases where the agricultural spray composition comprises the active ingredient, diluent, and pre-mix composition, the agricultural spray composition may comprise at least 95% water, e.g., at least 97%, at least 98%, or at least 99%, and at least 1 wt % pre-mix composition, e.g., at least 2 wt %, at least 3 wt %, or at least 4 wt %.

The present invention also relates to a process for treating an agricultural product. The process comprises the step of spraying the inventive agricultural spray composition on the agricultural product. Preferably, the spraying forms a plurality of droplets and the droplets have an average droplet size from 50 µm to 1000 µm, e.g., from 100 µm to 750 µm, from 100 µm to 600 µm, from 100 µm to 400 µm, 150 µm to 350 µm, or from 200 µm to 300 µm. In one embodiment, from 1 vol % to 10 vol %, e.g., from 2 vol % to 8 vol % or from 4 vol % to 6 vol %, of the droplets have a droplet size less than 105 µm. In one embodiment, no more than 10 vol %, e.g., no more than 8 vol % or no more than 6 vol %, of the droplets have a droplet size less than 105 µm. In one embodiment, more than 1 vol %, e.g., more than 2 vol % or more than 4 vol %, of the droplets have a droplet size less than 105 µm.

In one embodiment, the agricultural spray composition, when sprayed, yields a low number of driftable fines, e.g., droplets that are less than 150µ, e.g., less than 105µ in size (droplet diameter). Preferably, the weight percent of droplets less than 105µ in size is less than 10 wt %, e.g., less than 9 wt %, less than 8 wt %, less than 7 wt %, less than 6 wt %, less than 5 wt %, less than 4 wt %, less than 3 wt %, less than 2 wt %, or less than 1 wt %. In some embodiments, the agricultural spray composition, when sprayed, provides a high Dv10, which is the size (µm) at which 10% of the spray volume is of the reported size or smaller. Dv50 and Dv90 are similar statistics, but with different percentages, i.e., 50% and 90%, respectively). In some embodiments, the agricultural spray composition provides for a Dv50 greater than 125µ, e.g., greater than 150µ, greater than 175µ, greater than 200µ, greater than 250µ, greater than 260µ, greater than 270µ, greater than 275µ, or greater than 280µ. In some embodiments, the agricultural spray composition, when sprayed, provides a low relative span. Relative span is a measure of the width of the droplet size distribution, e.g., the ratio of difference between Dv90 and Dv10 to the Dv50. For example the agricultural spray composition may provide a relative span less than 1.5, e.g., less than 1.4, less than 1.3, less than 1.2, less than 1.1, less than 1.0, less than 0.95, less than 0.90, or less than 0.85.

The combination of polymer dispersion and plasticizer in the adjuvant provides for agricultural spray compositions that have beneficial combinations of features. For example, the agricultural spray compositions may droplets having a low weight percentage of driftable fines, a low relative span, and a high Dv10. For example, the agricultural spray composition, when sprayed, may yield droplets having less than 10 wt % droplets less than 105µ in size, a relative span less than 1.5. and a Dv50 greater than 125µ. As another example, the agricultural spray composition, when sprayed, may yield droplets having less than 7 wt % droplets less than 105µ in size, a relative span less than 1.2. and a Dv50 greater than 250µ. Other combinations of limits/ranges (as may be discussed individually herein) are contemplated. The individual limits/ranges discussed herein may be combined to describe other beneficial combination features, e.g., a combination of a relative span less than 1.2 and an evaporation rate ranging from 1.0% weight loss/min to 8% weight loss/min.

In some cases, conventional emulsifyable oil adjuvants, when utilized in an agricultural spray composition, may be able to achieve the preferred combination of a low weight percentage of driftable fines, a low relative span, and/or a high Dv10. Such products, however, form micro-emulsion droplets may become unstable and phase separate over a time. These droplets may also become too large to spray via agricultural spray nozzles. And the droplets diameter remains substantially constant over time. Also, in contrast to the inventive adjuvants, for emulsifyable oils, higher amounts of surfactants are needed to emulsify the oils. The higher loading of surfactants could potentially increase phytotoxicity and generate foam during mixing which may require the use of defoamers etc. that could add cost and complexity to the process. In contrast, the polymer dispersions according to this invention demonstrate superior performance, and also have much smaller particle diameters and do not require higher amounts of surfactants (due to the combination of polymer dispersion, plasticizer, and active ingredient).

In one embodiment, the agricultural composition has a slow evaporation rate. The evaporation rate may be measured using a Thermal gravimetric analysis (TGA) instrument, and the evaporation rate (of the droplets) may range from 1.0% weight loss/min to 8% weight loss/min, e.g., from 1.2% weight loss/min to 5% weight loss/min or from 1.2% weight loss/min to 2.5% weight loss/min. The drying time may range from 25 min to 100 min, e.g., from 35 min to 90 min, or from 40 min to 87 min. The dry time and evaporation rate may be measured using a TGA (Discovery TGA, TA Instruments). 40 µL of agriculture spray composition may be used. The temperature is ramped at 20° C./minute to 40° C., and the isotherm is collected for 75 minutes or until completely evaporated. Air is purged at a purge rate of 25 mL/min. The data are analyzed by using a linear fit to the evaporation data at 40° C. and using the slope to the linear fit as the average evaporation rate.

The surface tension of the droplets may decrease by less than 10 mN/m-min, e.g., less than 5 mN/m-min or less than 2 mN/m-min. As one example, an Attension Theta optical tensiometer with a manual syringe may be used to measure surface tension and contact angle. Data may be recorded with 40 frames/sec speed for 60 sec. Droplet sizes may be kept around 6 µm. If a pendant drop of 6 µm is not formed, the volumes of droplets may be increased accordingly.

The droplets may have an average contact angle from 35° to 75°, e.g., from 40° to 70°, or from 45° to 65°. As one example, contact angle may be determined using an Advanced Goniometer with PP texturized film as substrate.

The spread diameter may range from 4.5 mm to 7.0 mm, e.g., from 5 mm to 6.5 mm or from 5.5 mm to 6.0 mm. Optical Microscope with Coaxial Reflected Light. PP texturized film as substrate. 20 µL of sample was used The particle size distribution (PSD) measurements of the adjuvant may be conducted using a Mastersizer Microplus laser diffraction instrument from Malvern. The scatter data may be evaluated using the "Polydisperse Mie" model provided by Malvern. Particle sizes are given in µm. Particle fraction proportions were calculated from peak areas of the PSD curves.

The present invention also relates to a method for producing an agricultural spray composition. The method comprises the steps of providing the vinyl ester-based polymer dispersion and adding to the vinyl ester-based polymer dispersion a plasticizer to form the adjuvant. The method further comprises the step of adding to the adjuvant an active ingredient to form the agricultural spray composition. The adding step may comprise adding to the vinyl ester-based polymer dispersion at least 15 wt % plasticizer, based on the total weight of the spray adjuvant. A liquid carrier may also be added to the adjuvant.

Examples

The following examples are non-limiting.

Adjuvant Preparation

The adjuvants used in the examples below were prepared using the following method. The polymer dispersion was placed in a plastic container and agitated at 500 rpm. The plasticizer was slowly added to the polymer dispersion. Agitation was slowly increased during the course of plasticizer addition from 500 rpm to about 1000 rpm. Once all the plasticizer was incorporated, water was added to the mixture to lower its viscosity to a pourable consistency. A freeze-thaw additive was added to the adjuvant.

The solid content of the adjuvants was measured by heating 1 gram of the adjuvant at 110° C. for 1 hr. The solid content of the adjuvants varied between 55 and 60% and the pH between 4 and 5.5. Dur-O-Set C-310 and Dur-O-Set C-325 are colloid stabilized polyvinyl acetate homopolymers (PVAc), Dur-O-Set E130 is a colloid stabilized vinyl acetate and ethylene copolymer (VAE). Avicor 325 and 384 are non-ionic surfactant stabilized polyvinyl acrylic copolymer (PVA). Adjuvant formulations are shown in Table 1.

fate, aminated phosphoric acid, carboxylic acids, and undisclosed spray deposition aids. Hel-fire as received had a pH of 0.65-0.75. Hel-fire was neutralized with 20% NaOH to a pH about 2.0 prior to making the pre-mix formulation. The urea sulfate received from Peach State lab contained urea sulfate and had a pH of 2.6 and was used as is. The components were mixed in a plastic container in the order shown in the Tables 2a and 2b. The first component in each Table was placed in the plastic container and agitated at 300 rpm. The mixing was achieved using a lightning mixer. Each of the additional ingredients was added slowly to the mixture. The solid content of the final US-APC was between 45 and 50% and the pH was between 2 and 3.

The prepared US-APCs were tested for stability. Samples were split into two labeled plastic containers each covered with a tight lid. For at least two weeks, one of the containers was aged at 25° C. and the other was aged in an oven maintained at 40° C. The containers were visually inspected daily for stability. US-APCs were deemed stable if after 2 weeks upon visual inspection there were no signs of macro-separation, which could include presence of solid gel, separation into distinct layers, particulates or significant settling. Significant settling is defined as settling that requires a mechanical device to re-disperse the settled material.

The prepared US-APCs were tested for dispersion. At the end of the 2 week aging period, aging was stopped by removing the sample from the oven. The warm containers were brought to room temperature. Once a final visual

TABLE 1

Adjuvant Formulations

| | Adj. 1 | Adj. 2 | Adj. 3 | Adj. 4 | Adj. 5 | Adj. 6 | Adj. 7 | Adj. 8 | Adj. 9 |
|---|---|---|---|---|---|---|---|---|---|
| DOS C-335 (polymer dispersion) | 45 | | | | | | | | |
| Avicor 384 (polymer dispersion) | | 60 | | | | | | | |
| Avicor 325 (polymer dispersion) | 15 | | 60 | 60 | | | | | |
| DOS E-130 (polymer dispersion) | | | | | 60 | | | | |
| DOS C-310 (polymer dispersion) | | | | | | 60 | 76 | 92 | 100 |
| Vikoflex 7170[1] (soybean oil plasticizer) | 40 | 40 | 40 | 20 | 35 | 40 | 30 | 20 | 10 |
| Water | 22 | 22 | 22 | 8 | 17.5 | 22 | 14 | 6 | 0 |
| Makon TSP 16[2] (surfactant) | 0.3 | 0.3 | 0.3 | 0.3 | 0.45 | 0.3 | 0.3 | 0.3 | 0.3 |
| Total | 122.3 | 122.3 | 122.3 | 88.3 | 112.95 | 122.3 | 120.3 | 118.3 | 110.3 |

[1]Arkema, Inc.
[2]Stepan Company

Urea Sulfate Pre-Mix Preparation

Urea Sulfate water conditioner based agricultural pre-mix compositions ("US-APC") were prepared by blending urea sulfate with adjuvants and other additives such as surfactants and co-solvents such as propylene glycol. The urea sulfate water conditioner was from Helena Chemical Company or from Peach State Labs, LLC. Helena Chemical Company sells urea sulfate water conditioner under the trade name Hel-Fire®. The Hel-fire contained, in addition to urea sulinspection was performed, the contents of each container were tested for dispersion in water. This dispersion test is intended to mimic mixing in a spray tank prior to spray application to crops. In a plastic container, 0.1-5 wt. % of the US-APC was mixed with 95-99.9 wt. % of Florence, Ky. city water (In 2015, total hardness of the Northern Kentucky water district water averaged about 129 ppm). The US-APC was deemed to pass the dispersion test, if it readily dispersed in water with minimum agitation (less than 100 rpm lightnin mixer speed) and without macro-separation. Macro-separation in this case would result in visible particulates, gels or significant settled material. The US-APCs shown in Tables 2a and 2b were stable at the end of the two week period both at 25° C. and 40° C. and passed the dispersion test by forming a homogeneous dispersion at the use rates mentioned above. The stability and dispersion test results are shown in the Tables 2a and 2b.

TABLE 2a

Urea Sulfate Pre-Mix Compositions

| | Pre-mix 1 | Pre-mix 2 | Pre-mix 3 | Pre-mix 4 | Pre-mix 5 | Pre-mix 6 | Pre-mix 7 |
|---|---|---|---|---|---|---|---|
| Adj. 1 | 16.6 | 12.5 | 20 | 20 | | | |
| Adj. 2 | | | | | 30 | | |
| Adj. 3 | | | | | | 30 | |
| Adj. 4 | | | | | | | 30 |
| Water | | 37.5 | 15.5 | 12.5 | 14 | 14 | 14 |
| Hel-Fire [4] (water conditioner) | 41.7 | 50 | 50 | 50 | 50 | 50 | 50 |
| PG | 41.7 | | 3 | 3 | | | |
| Span 80[3] (surfactant) | | | 3.5 | 3.5 | | | |
| Tween 80[3] (surfactant) | | | 8 | 11 | | | |
| Span 85[3] (surfactant) | | | | | 2.31 | | |
| Synperonic PE/L121[3] (surfactant) | | | | | 3.69 | 6 | 6 |
| Total | 100 | 100 | 100 | 100 | 100 | 100 | 100 |
| Stability at 25° C. (2 weeks) | Yes | Yes | Yes | Yes | Yes | Yes | Yes |
| Stability at 40° C. (2 weeks) | Yes | Yes | Yes | Yes | Yes | Yes | Yes |
| Dispersion at 2 oz/10 gal | Disperses readily. No particulates | Disperses readily. No particulates | Disperses readily. No particulates | Disperses readily. No particulates | Disperses readily. No particulates | Disperses readily. No particulates | Disperses readily. No particulates |

[3] Croda, Inc.
[4] Hel-fire (Helena Chemical Company)

TABLE 2b

Urea Sulfate Pre-Mix Compositions

| | Pre-mix 8 | Pre-mix 9 | Pre-mix 10 | Pre-mix 11 | Pre-mix 12 | Pre-mix 13 | Pre-mix 14 |
|---|---|---|---|---|---|---|---|
| Adj. 3 | 30 | 40 | | 30 | 20 | | |
| Adj. 4 | | | 40 | | | 30 | 30 |
| Hel-Fire[4] (water conditioner) | 50 | 50 | 50 | | 50 | 50 | 50 |
| Peach State Lab [5] (water conditioner) | | | | 50 | | | |
| Span 85 (surfactant) | | | | | | | 4 |
| Synperonic PE/L121 (surfactant) | 4 | 6 | 6 | 8 | 20 | 20 | 2 |
| Water | 16 | 4 | 4 | 12 | 10 | | 14 |
| Total | 100 | 100 | 100 | 100 | 100 | 100 | 100 |
| Stability at 25° C. (2 weeks) | Yes | Yes | Yes | Yes | Yes | Yes | Yes |
| Stability at 40° C. (2 weeks) | Yes | Yes | Yes | Yes | Yes | Yes | Yes |
| Dispersion at 2 oz/10 gal | Disperses readily. No particulates | Disperses readily. No particulates | Disperses readily. No particulates | Disperses readily. No particulates | Disperses readily. No particulates | Disperses readily. No particulates | Disperses readily. No particulates |

[5] Peach State Lab, LLC - Urea Sulfate pH = 2.6

Ammonium Sulfate Pre-Mix Preparation

AMS containing Agricultural Pre-mix Compositions ("AMS-APC") were prepared by blending either solid ammonium sulfate or 40 wt. % ammonium sulfate solution in water with adjuvant and other additives such as surfactants and co-solvents such as propylene glycol. The AMS-APCs were prepared using the adjuvants shown in Table 1 and the adjuvant procedure described above. The components were mixed in a plastic container in the order shown in the Tables 3a and 3b. The first component in each Table was placed in the plastic container and agitated at 300 rpm. The mixing was achieved using a lightnin mixer. Each of the additional ingredients was added slowly to the vortex.

The prepared US-APCs were tested for stability. The samples were split into two labeled plastic containers each covered with a tight lid. For at least two weeks, one of the containers was aged at 25° C. and the other was aged in an oven maintained at 40° C. The containers were visually inspected daily for stability. US-APCs were deemed stable if after 2 weeks upon visual inspection there were no signs of macro-separation, which could include presence of solid gel, separation into distinct layers, particulates or significant settling. Significant settling is defined as settling that requires a mechanical device to re-disperse the settled material.

The prepared US-APCs were tested for dispersion. At the end of the 2 week aging period, aging was stopped by removing the sample from the oven. The warm containers were brought to room temperature. Once a final visual inspection was performed, the contents of each container were tested for dispersion in water. This dispersion test is indented to mimic mixing in a spray tank prior to spray application to plants. In a plastic container, 0.1-5 wt. % of the AMS-APC was mixed with 95-99.9 wt. % of city water.[9] The AMS-APC was deemed to pass the dispersion test, if it readily dispersed in water with minimum agitation (less than 100 rpm lightnin mixer speed) and without macro-separation. Macro-separation in this case would result in visible particulates, gels or significant settled material. The stability and dispersion test results are shown in the Tables 3a and 3b.

The AMS-APCs shown in Tables 3a and 3b were stable at the end of the two week period both at 25° C. and 40° C. As noted in Tables 3a and 3b, many of them showed a cloudy layer or some settling, however the cloudy layer or settling could be easily re-dispersed easily upon gentle stirring. Thus, these samples were deemed to be stable. All the formulations listed in Table 3a and 3b passed the dispersion test by forming a homogeneous dispersion at the use rates mentioned above.

TABLE 3a

Ammonium Sulfate Pre-Mix Compositions

|  | Pre-mix 15 | Pre-mix 16 | Pre-mix 17 | Pre-mix 18 | Pre-mix 19 |
|---|---|---|---|---|---|
| Adj. 5 | 3 | 3 | 3 | 6 |  |
| Adj. 6 |  |  |  |  | 6 |
| 40 wt % AMS solution[8] (water conditioner) |  | 24 |  |  |  |
| AMS solid (water conditioner) | 9.5 |  | 9.5 | 12 | 7.5 |
| Propylene glycol |  |  |  | 3 |  |
| Rhodaline 4188[6] (surfactant) | 10 | 15 | 15 |  |  |
| Disponil 3065[7] (surfactant) |  |  | 5 |  |  |
| Polystep B-29[2] (surfactant) |  |  |  | 65 | 40 |
| 5% NaOH | 3.5 | 5 | 5 |  |  |
| Water | 74 | 53 | 62.5 | 14 | 46.5 |
| Total | 100 | 100 | 99.9 | 100 | 100 |
| Stability at 25° C. (2 weeks) | Cloudy layer at bottom | Cloudy layer at bottom | Cloudy layer at top | Some separation | Some settling |
| Stability at 40° C. (2 weeks) | Some settling | Some settling | Cloudy layer at top | Some settling | Some settling |
| Dispersion at 2 oz/ 10 gal | Disperses readily. No particulates | Disperses readily. No particulates | Disperses readily. No particulates | Disperses readily. No particulates | Disperses readily. No particulates |

[6]Solvay USA, Inc
[7]BASF Corporation
[8]40% AMS solution was prepared by dissolving 40 g of solid ammonium sulfate in 60 grams of water
[9]Water hardness of Boone County, is approximately 129 ppm TABLE 3b Ammonium Sulfate Pre-Mix Compositions

|  | Pre-mix 20 | Pre-mix 21 | Pre-mix 22 | Pre-mix 23 | Pre-mix 24 | Pre-mix 25 | Pre-mix 26 |
|---|---|---|---|---|---|---|---|
| Adj. 5 | 3 | 6 | 6 |  |  |  |  |
| Adj. 7 |  |  |  |  |  | 6 |  |
| Adj. 8 |  |  |  |  |  |  | 6 |
| Adj. 9 |  |  |  | 6 | 6 |  |  |
| AMS solid (water conditioner) | 9.5 | 7.75 | 8.75 | 9.5 | 7.5 | 9.5 | 9.5 |

TABLE 3b-continued

Ammonium Sulfate Pre-Mix Compositions

| | Pre-mix 20 | Pre-mix 21 | Pre-mix 22 | Pre-mix 23 | Pre-mix 24 | Pre-mix 25 | Pre-mix 26 |
|---|---|---|---|---|---|---|---|
| Propylene glycol | | 3 | 3 | | | | |
| SXS, 40% solution sodium xylene sulfonate (sufactant) | 31.25 | 31.25 | 31.25 | 40 | 40 | 40 | 40 |
| Disponil 3065 (surfactant) | 5 | | | | | | |
| Water | 51.25 | 52 | 51 | 44.5 | 46.5 | 44.5 | 44.5 |
| Total | 100 | 100 | 100 | 100 | 100 | 100 | 100 |
| Stability at 25° C. (2 weeks) | Cloudy layer at bottom | Some settling | Some settling | Some settling | Some settling | Some settling | Some settling |
| Stability at 40° C. (2 weeks) | Some settling | Some settling | Some settling | Some settling | Some settling | Some settling | Some settling |
| Dispersion at 2 oz/10 gal | Disperses readily. No particulates | Disperses readily. No particulates | Disperses readily. No particulates | Disperses readily. No particulates | Disperses readily. No particulates | Disperses readily. No particulates | Disperses readily. No particulates |

While the invention has been described in detail, modifications within the spirit and scope of the invention will be readily apparent to those of skill in the art. It should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of ordinary skill in the art. Furthermore, those of ordinary skill in the art will appreciate that the foregoing description is by way of example only, and is not intended to limit the invention.

We claim:

1. An agricultural spray pre-mix composition, comprising:
   from 0.01 wt % to 40 wt %, based on the total weight of the pre-mix composition, of an agricultural spray adjuvant comprising:
      a vinyl ester-based or vinyl acrylate-based polymer dispersion; and
      greater than 15 wt %, based on total weight of the adjuvant, of a plasticizer; and
   from 1 wt % to 50 wt %, based on the total weight of the pre-mix composition, of a water conditioning agent.

2. The pre-mix composition of claim 1, wherein the water conditioning agent comprises a compound selected from nitrogen-containing sulfates, carboxylic acids, phosphate salts, and mixtures thereof.

3. The pre-mix composition of claim 1, wherein the pre-mix composition comprises a surfactant present in an amount less than 15 wt % based on the total weight of the pre-mix composition.

4. The pre-mix composition of claim 1, wherein the adjuvant comprises a surfactant present in an amount less than 10 wt % based on the total weight of the adjuvant.

5. The pre-mix composition of claim 1, wherein the pre-mix composition shows a non-Newtonian rheology having a viscosity less than about 150 cp, as measured by a rotational rheometer.

6. The pre-mix composition of claim 1, further comprising a surfactant having a hydrophilic lipophilic balance less than 15.

7. The pre-mix composition of claim 1, further comprising a surfactant comprising a compound selected from the group consisting of oleates, polyoxyethylene/polyoxypropylene block copolymers, glycols, fatty acid esters, alcohol ethoxylates, sulfates, sulfonates, sulfonic acids, and mixtures thereof.

8. The pre-mix composition of claim 1, wherein the pre-mix composition, when combined with water at a weight ratio of at least 95:1, has a viscosity less than 5 cp as measured by a rotational rheometer.

9. The pre-mix composition of claim 1, wherein after at least two weeks of storage at 25° C. the pre-mix composition shows substantially no macro separation.

10. The pre-mix composition of claim 1, wherein, when mixed with water at a volume ratio of 0.05 ounces/gallon to 1 ounce/gallon and after at least two weeks of storage at 25° C., the resultant composition is a homogeneous dispersion.

11. The pre-mix composition of claim 1, wherein the plasticizer is present in an amount from 15 wt % to 70 wt %, based on the total weight of the pre-mix composition.

12. The pre-mix composition of claim 1, wherein the plasticizer is selected from the group consisting of a triethylene glycol diester, a polyalkylene glycol, triethylene glycol di-2-ethylhexoate, a polyether polyol, an ester of canola oil, an ester of castor oil, 2,2,4-trimethyl-1,3-pentanediol monoisobutyrate, a phthalate, an adipic acid polyesters, a trimellitate, an adipate, an epoxy ester, a polyetherester, a benzoate, a dipropylene glycol dibenzoate, a diethylene glycol dibenzoate, epoxidized methyl ester of soy oil, methyl ester of soy oil, and mixtures thereof.

13. A process for producing an agricultural spray composition, comprising:
   providing an agricultural spray pre-mix composition; and
   adding to the agricultural spray pre-mix composition an active ingredient to form the agricultural spray composition,
   wherein the agricultural spray pre-mix composition comprises:
      from 0.01 wt % to 40 wt %, based on the total weight of the pre-mix composition, of an agricultural spray adjuvant comprising:
         a vinyl ester-based or vinyl acrylate-based polymer dispersion; and greater than 15 wt %, based on total weight of the adjuvant, of a plasticizer; and from 1 wt % to 50 wt %, based on the total weight of the pre-mix composition, of a water conditioning agent.

14. The process of claim 13, wherein the active ingredient is selected from the group consisting of herbicides, pesticides, fungicides, insecticides, acaricides, nematocides, foliar nutrients, defoliants, plant growth regulators, molluscidcides and mixtures thereof.

15. The process of claim 13, wherein the adjuvant and the water conditioning agent are combined prior to the addition of the active ingredient.

16. The process of claim 13, wherein the plasticizer is selected from the group consisting of a triethylene glycol diester, a polyalkylene glycol, triethylene glycol di-2-ethylhexoate, a polyether polyol, an ester of canola oil, an ester of castor oil, 2,2,4-trimethyl-1,3-pentanediol monoisobutyrate, a phthalate, an adipic acid polyesters, a trimellitate, an adipate, an epoxy ester, a polyetherester, a benzoate, a dipropylene glycol dibenzoate, a diethylene glycol dibenzoate, epoxidized methyl ester of soy oil, methyl ester of soy oil, and a mixture of two more thereof.

17. An agricultural spray composition comprising:
an active ingredient; and
a pre-mix composition comprising:
from 1 wt % to 50 wt %, based on the total weight of the pre-mix composition, of a water conditioning agent; and
from 0.01 wt % to 40 wt %, based on the total weight of the pre-mix composition, of an agricultural spray adjuvant comprising:
a vinyl ester-based or vinyl acrylate-based polymer dispersion; and
greater than 15 wt %, based on total weight of the adjuvant, of a plasticizer.

18. The process of claim 17, wherein the active ingredient is selected from the group consisting of herbicides, pesticides, fungicides, insecticides, acaricides, nematocides, foliar nutrients, defoliants, plant growth regulators, molluscidcides and mixtures thereof.

19. A process for treating an agricultural product, comprising:
spraying on the agricultural product an agricultural spray composition comprising:
an active ingredient; and
a pre-mix composition comprising:
from 1 wt % to 50 wt %, based on the total weight of the pre-mix composition, of a water conditioning agent and
from 0.01 wt % to 40 wt %, based on the total weight of the pre-mix composition, of an agricultural spray adjuvant comprising:
a vinyl ester-based or vinyl acrylate-based polymer dispersion; and
greater than 15 wt %, based on total weight of the adjuvant, of a plasticizer.

20. The process of claim 19, wherein the spraying forms droplets and less than 10 vol % of the droplets have a droplet size less than 105 μm, when sprayed using a flat fan nozzle.

* * * * *